(12) United States Patent
De Souza et al.

(10) Patent No.: US 8,772,544 B2
(45) Date of Patent: Jul. 8, 2014

(54) PROCESS FOR THE PRODUCTION OF BIMATOPROST

(75) Inventors: Dominic De Souza, Kundl (AT); Martin Albert, Kundl (AT); Hubert Sturm, Kundl (AT)

(73) Assignee: Sandoz AG, Basel (CH)

( * ) Notice: Subject to any disclaimer, the term of this patent is extended or adjusted under 35 U.S.C. 154(b) by 193 days.

(21) Appl. No.: 12/999,112

(22) PCT Filed: Jun. 10, 2009

(86) PCT No.: PCT/EP2009/057186
§ 371 (c)(1),
(2), (4) Date: Feb. 23, 2011

(87) PCT Pub. No.: WO2009/153206
PCT Pub. Date: Dec. 23, 2009

(65) Prior Publication Data
US 2011/0178340 A1    Jul. 21, 2011

(30) Foreign Application Priority Data
Jun. 20, 2008    (EP) ..................................... 08158675

(51) Int. Cl.
C07C 233/05    (2006.01)
(52) U.S. Cl.
USPC .......................................... 564/170; 564/171
(58) Field of Classification Search
USPC ................................................ 564/170, 171
See application file for complete search history.

(56) References Cited

U.S. PATENT DOCUMENTS

| 5,359,095 A | 10/1994 | Resul |
| 5,698,733 A | 12/1997 | Hellberg et al. |
| 2005/0209337 A1 | 9/2005 | Gutman |
| 2007/0167641 A1 | 7/2007 | Wei et al. |

FOREIGN PATENT DOCUMENTS

| EP | 364417 A1 | 4/1990 |
| WO | 9002553 A | 3/1990 |
| WO | 9406433 A1 | 3/1994 |
| WO | 0155101 A2 | 8/2001 |
| WO | 2002096898 A2 | 12/2002 |
| WO | 2003074481 A2 | 9/2003 |
| WO | 2005058812 A | 6/2005 |
| WO | 2006094294 A2 | 9/2006 |

OTHER PUBLICATIONS

International Search Report and Written Opinion (completed Jul. 30, 2009).
Corey et al, W. J. Am. Chem. Soc. 1969, 91, 5675-5677.
Corey et al., T. K. J. Am. Chem. Soc. 1970, 92, 2586-2587.

*Primary Examiner* — Shailendra Kumar
(74) *Attorney, Agent, or Firm* — Jeffrey S. Melcher; Manelli Selter PLLC

(57) ABSTRACT

The present invention relates to a process for the purification of crude bimatoprost to obtain pure bimatoprost comprising a chromatography, preferably a chromatography using an achiral stationary phase and an eluent comprising an alcohol and an apolar solvent; and crystallization of the product obtained the chromatography to obtain pure bimatoprost.

7 Claims, 2 Drawing Sheets

PROCESS FOR THE PRODUCTION OF BIMATOPROST

CROSS-REFERENCE TO RELATED APPLICATIONS

This application is a national stage entry under 35 U.S.C. 371 of International Application No. PCT/EP2009/057186, filed 10 Jun. 2009, designating the United States. This application claims foreign priority under 35 U.S.C. 119 and 365 to European Patent Application No. 08158675.2, filed 20 Jun. 2008.

FIELD OF THE INVENTION

The present invention relates to an improved process for the production of prostaglandins and prostaglandin analogs. In particular, this invention relates to the production of a prostaglandin derivative of the $PGF_{2\alpha}$-series, namely bimatoprost, which is an active pharmaceutical ingredient used for the reduction of elevated intra-ocular pressure in patients with glaucoma and ocular hypertension. The invention describes a process which gives bimatoprost in high purity.

BACKGROUND OF THE INVENTION

Prostaglandins are a family of biologically active compounds that are found in virtually all tissues and organs. These naturally occurring prostaglandis have extremely complex biological functions (e.g. stimulation of smooth muscles, dilation of smaller arteries and bronchi, lowering blood pressure, etc.). Synthetic prostaglandins are for example clinically used to induce childbirth or abortion, to prevent and treat peptic ulcers, to treat pulmonary hypertension, in treatment of glaucoma and ocular hypertension.

Prostaglandin $F_{2\alpha}$ (($PGF_{2\alpha}$-(Z)-7-((1R,2R,3R,5S)-3,5-dihydroxy-2-((S,E)-3-hydroxyoct-1-enyl)cyclopentyl)hept-5-enoic acid)) has the structure shown below:

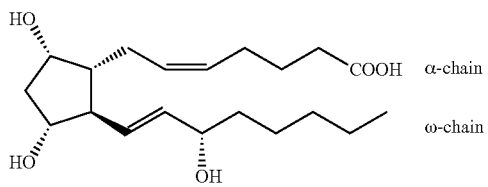

The $PGF_{2\alpha}$-derivatives are thus characterized by two hydroxyl groups in cis configuration relative to the cyclopentane ring, and two side chains in a trans configuration relative to each other. Analogs of $PGF_{2\alpha}$ may have a different number of double bonds in the side chains and the substituents along the side chains as well as the length of the side chains may vary. The Z-configured double bond in the α-chain is a common feature in pharmaceutically active $PGF_{2\alpha}$ analogs, whereas the double bond in the ω-chain may be missing (e.g. latanoprost and unoprostone). Particularly useful are derivatives with a ω-chain bearing a phenyl substituent and wherein the α-chain is an ester or an amide.

Examples for such $PGF_{2\alpha}$ derivatives having therapeutic use are latanoprost (general formula (II)), travoprost (general formula (III)), and bimatoprost (general formula (I)). Bimatoprost, in contrast to latanoprost and travoprost, has an amide function, which influences the polarity of the molecule in a way that purification strategies utilized for latanoprost and travoprost can not be applied.

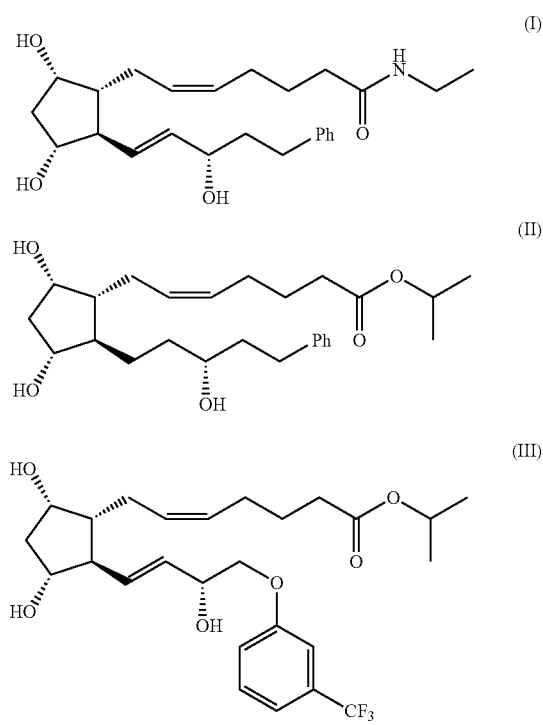

$PGF_{2\alpha}$-analogs for use in treatment of glaucoma and ocular hypertension are described for example in EP 0 364 417 A1 (Pharmacia AB). In EP 0 364 417 A1, a number of $PGF_{2\alpha}$-analogs with variations in the ω-chain are described. The synthesis disclosed follows the original route of Corey et al. (Corey, E. J.; Weinshenker, N. M.; Schaaf, T. K.; Huber, W. *J. Am. Chem. Soc.* 1969, 91, 5675-5677; Corey, E. J.; Noyori, R.; Schaaf, T. K. *J. Am. Chem. Soc.* 1970, 92, 2586-2587) with some modifications and is shown in scheme 1 for the preparation of 17-phenyl-18,19,20-trinor-$PGF_{2\alpha}$-isopropy ester.

The starting material disclosed in EP 0 364 417 A1 is commercially available p-phenyl-benzoyl (PPB) protected Corey lactone (1), which is converted into the corresponding aldehyde (2) by oxidation using DCC/DMSO. Compound (2) is not isolated but reacted in solution with an appropriate phosphonium salt to give intermediate (3). Reduction of the ketone in compound (3) forms the corresponding alcohol (4) as a mixture of diastereomers. After deprotection to form diol (5) the lactone is selectively reduced to the lactol (6) which was purified using column chromatography. A subsequent Wittig reaction forms acid (7) which is converted into the desired product (8) by esterification using isopropyl iodide.

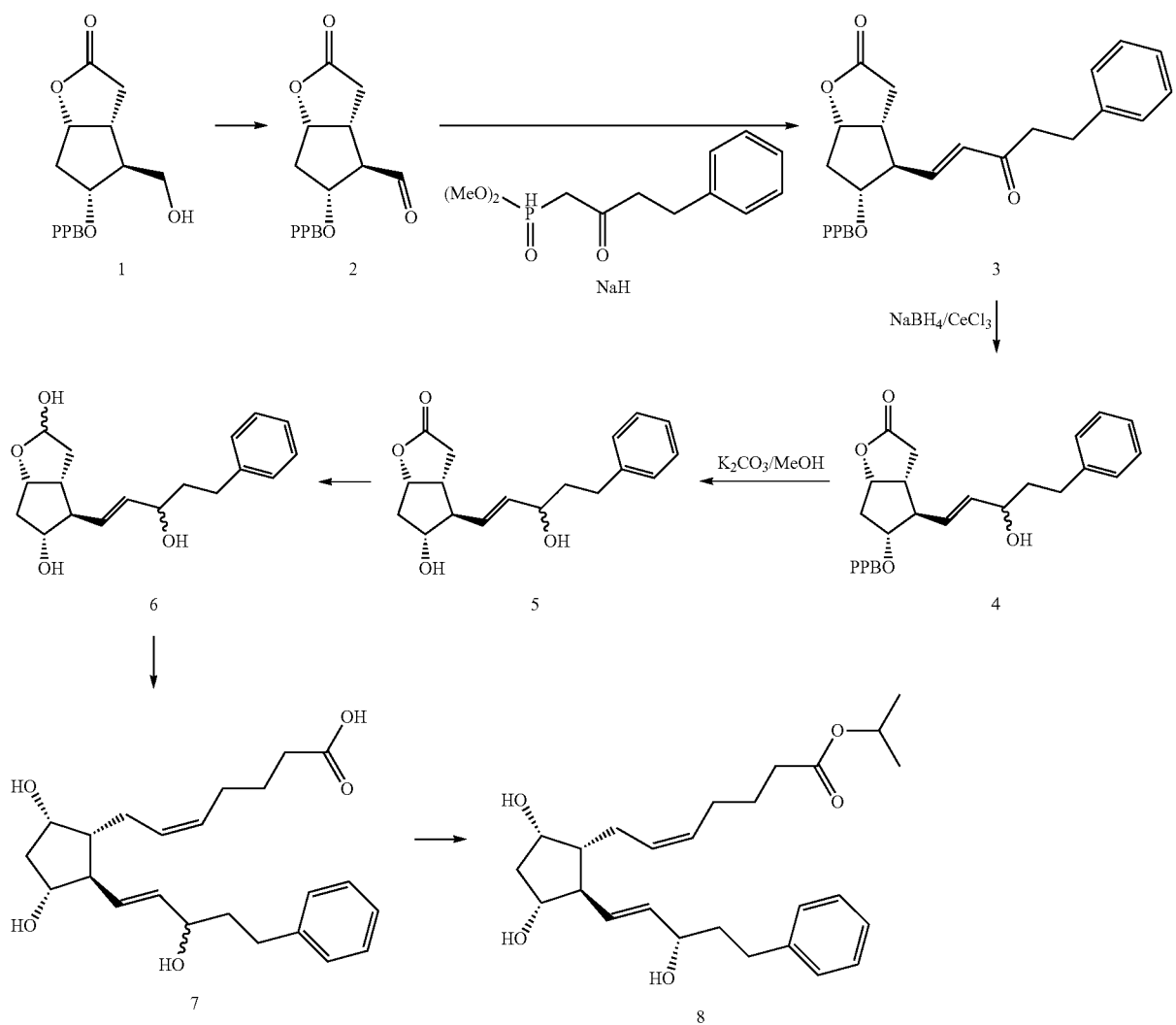
Scheme 1
In WO 94/06433 (Allergan) the conversion of acid (7) to bimatoprost using a two step synthesis is described. The first step is an esterification using methyl iodide, which is followed by an amide formation using ethylamine (scheme 2).
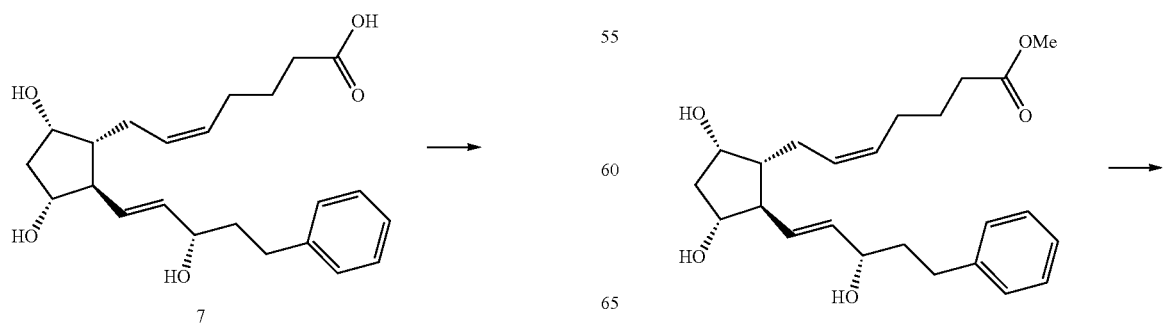
Scheme 2
-continued

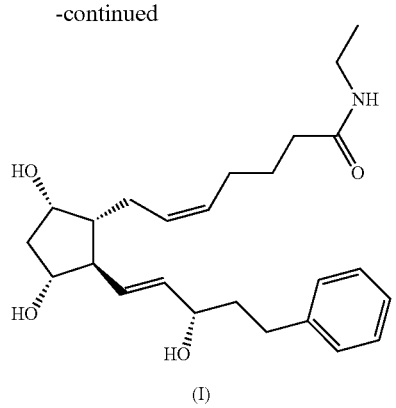

An improved synthesis for such 13,14-dihydro PGF$_{2\alpha}$-analogs is described in U.S. Pat. No. 5,359,095 (Pharmacia AB; scheme 3). As the original reduction of the ketone 3 only gave 37% yield of the desired 15S-alcohol (9), L-selectride was used as reducing agent, improving the diastereoselectivity of the reduction and increasing the yield of (9) to 60%. Additionally, it had been found that the allylic alcohol in compound (9) is deoxygenated on hydrogenation of the double bond over palladium catalyst. Therefore, protection of the allylic alcohol (as tetrahydropyranylether) seemed to be necessary.

However, this sequence for the preparation of latanoprost involves two additional steps (protection/deprotection) and insufficiently solves the problem regarding the diastereoselectivity of the reduction from (3) to (9). The synthesis of bimatoprost is not disclosed in this patent application.

Scheme 3

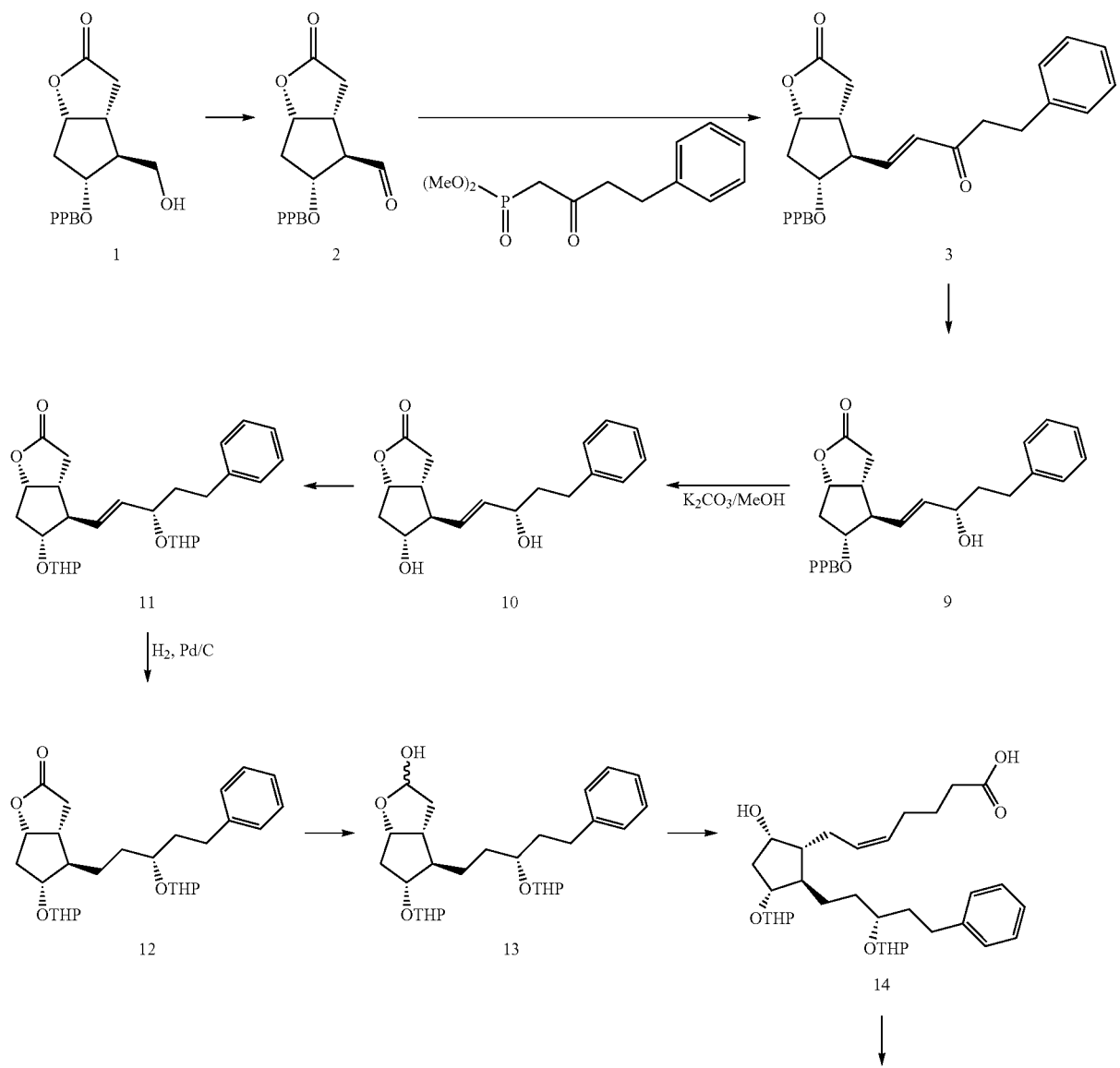

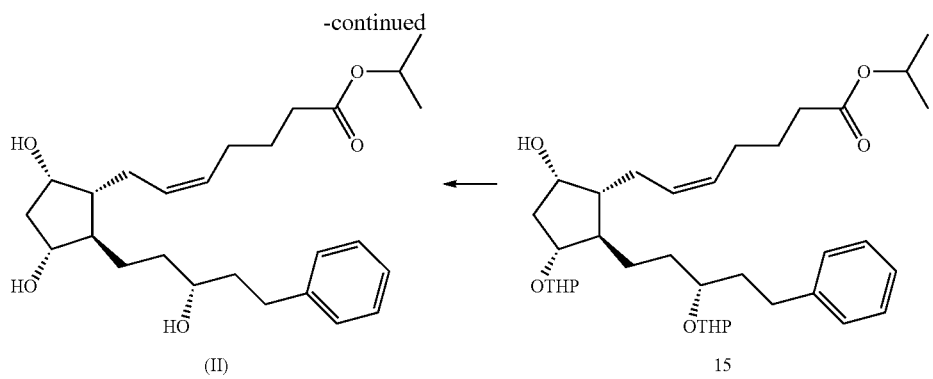

(II)    15

In U.S. Pat. No. 5,698,733 (Alcon) a further process for the stereoselective reduction of benzoyl-protected enone (16) is described using (−)-B-chlorodiisopinocamphenylborane [(−)-DIP-Cl]. The desired 15S-alcohol (17), which is the chemical equivalent of compound (9), is obtained with a diastereomeric excess (de) of 92% (scheme 4).

Scheme 4

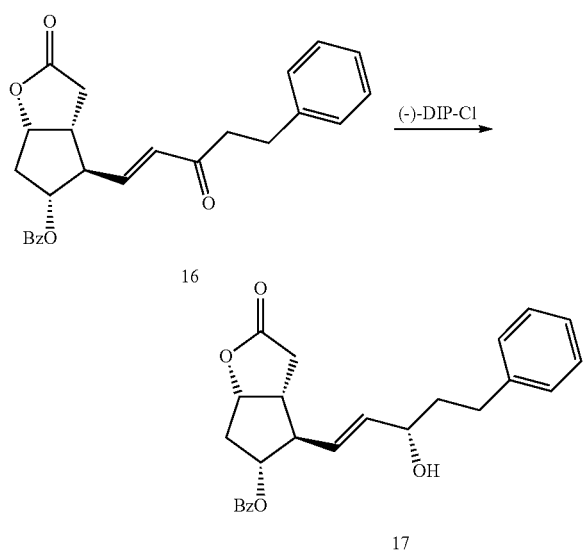

International patent application WO 2006/094294 (Teva) describes another methodology to deplete the unwanted 15R-isomer using enzymatic acylation or enzymatic ester hydrolysis.

Patent applications WO 2002/096898 (Resolution Chemicals) and US 2007/0167641 (Chirogate) describe the use of silyl protecting groups in the preparation of $PGF_{2\alpha}$-analogs.

Patent applications WO 01/55101 (Finetech) and WO 2002/096868 (Finetech) make of use of THP (tetrahydropyranyl) or THP and PPB (p-phenyl-benzoyl) protecting groups and describe the recovery of the unwanted C-15 epimer by an oxidation-reduction sequence.

In WO 2003/074481 (Allergan) the coupling of protected lactol (18) with heptanoic derivative (23) is described (scheme 5, Z represents a protecting group and the dotted line in the formula represents the presence or absence of a double bond). The advantage of the invention is that the complete α-side chain is introduced in one step. However, as no experimental details are given the process can not be compared with the prior art. It is mentioned that impurities in crude bimatoprost are limited to less than 8% thereby suggesting a high level of impurities generated during the process. The process requires the use of protecting groups making the reaction sequence lengthy.

Scheme 5

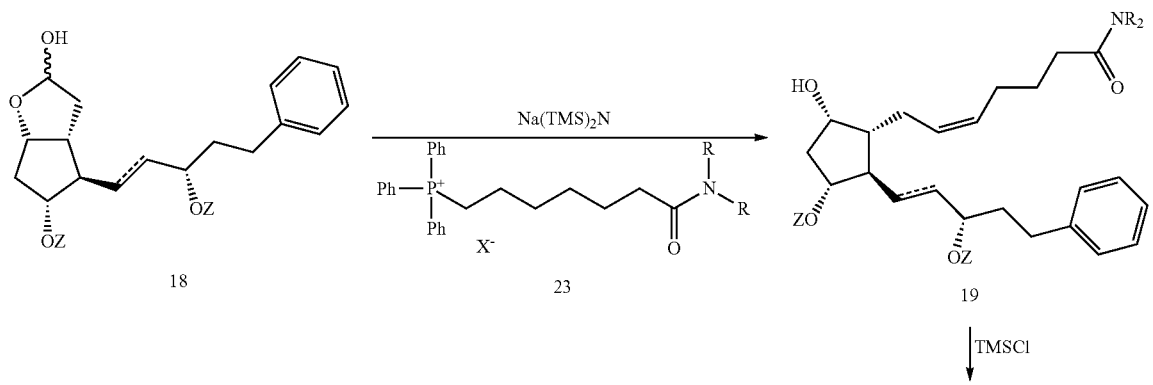

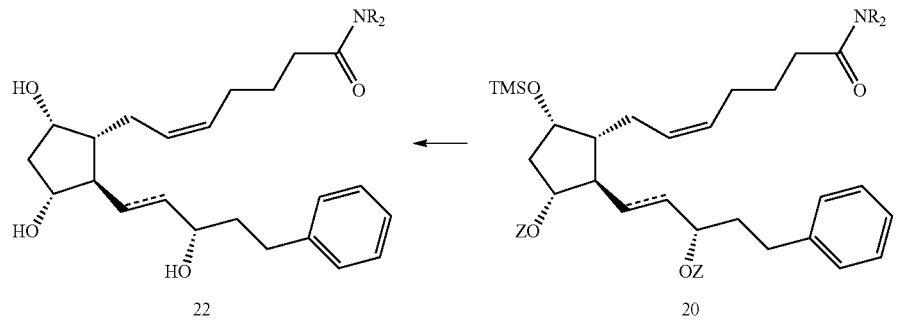

The processes described in the state of the art have the drawback that the α-chain is introduced using the Wittig reagent derived from 5-triphenylphosphoniopentanoic acid to give the corresponding acid which has to be converted into an ester or an amid in a further step to obtain the desired compound. In the case of bimatoprost, the introduction of the amide functionality out of the corresponding acid needs two steps and requires long reaction times or that elaborate protecting group strategies are used. The isolation of many intermediates is necessary and the process is laborious and less efficient. Furthermore, bimatoprost is obtained in insufficient purity.

OBJECTS OF THE INVENTION

It is an object of the invention to provide a novel and improved process for the preparation of bimatoprost in good yields, in large amounts and with high purity.

It is also an object of the invention to provide a process for the preparation of bimatoprost that involves a minimum amount of isolated intermediates and therefore simplifies the process.

A further aspect of the invention is to provide a method to obtain high purity bimatoprost.

SUMMARY OF THE INVENTION

The above objects are achieved by a process for the purification of crude bimatoprost comprising at least the steps of
(a) chromatography and
(b) crystallization of the product obtained in step (a).

In the context of the present invention, the term "crude bimatoprost" denotes a composition comprising bimatoprost and the impurities 15R-bimatoprost (29) and 5,6-trans-bimatoprost (30), respectively in an amount of more than 0.7% in total of any combination of 15R-bimatoprost (29) and 5,6-trans-bimatoprost (30), based on the weight of bimatoprost. The amount refers to the sum of 15R-bimatoprost (29) and 5,6-trans-bimatoprost (30). 15R-bimatoprost (29) and 5,6-trans-bimatoprost (30) are found as impurities in bimatoprost which is prepared according to any of the prior art processes and which is available on the market.

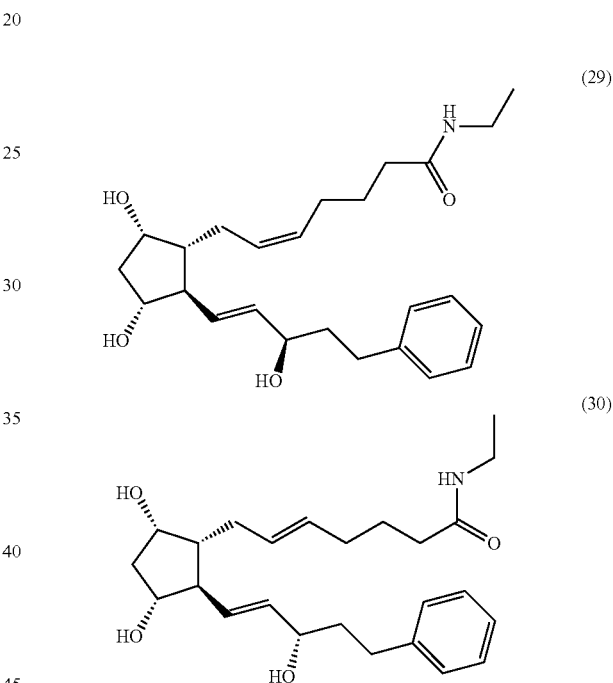

In the context of the present invention, the term "pure bimatoprost" denotes a composition comprising bimatoprost and the impurities 15R-bimatoprost (29) and 5,6-trans-bimatoprost (30), respectively in an amount of less than 0.7% in total, for example from 0.01% to 0.7% in total, of any combination of 15R-bimatoprost (29) and 5,6-trans-bimatoprost (30), preferably less than 0.5% in total, for example from 0.01% to 0.5% in total, most preferably less than 0.2% in total, for example from 0.01% to 0.2% in total, based on the weight of bimatoprost.

As a general observation, the product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of an API, such as bimatoprost, it must be analyzed for purity, typically, by HPLC or TLC analysis, to determine if it is suitable for continued processing and, ultimately, for use in a pharmaceutical product. The API need not be absolutely pure, as absolute purity is a theoretical ideal that is typically unattainable. Rather, purity standards are set with the intention of ensuring that an API is as free of impurities as possible, and, thus, is as safe as possible for clinical use. It is not unusual that national guidelines recommend that the amounts of some impurities be limited to less than 0.1%.

It was now found that the two impurities 15R-bimatoprost (29) and 5,6-trans-bimatoprost (30) can be removed by the process according to the present invention to a level below 0.7% in total, for example from 0.01% to 0.7% in total, of any combination of 15R-bimatoprost (29) and 5,6-trans-bimatoprost (30), preferably below 0.5% in total, for example from 0.01% to 0.5% in total, most preferably below 0.2% in total, for example from 0.01% to 0.2% in total, by a combination of chromatography, in particular on an achiral stationary phase using an alcohol and an apolar solvent as eluent, and one crystallisation step.

According to the present invention, crude bimatoprost can be obtained according to any process known to the person skilled in the art.

According to a further embodiment, the present invention relates to a process for the preparation of crude bimatoprost comprising at least step (i)

(i) reaction of a compound of formula (6)

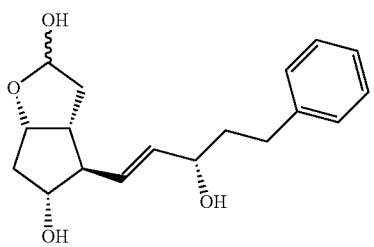

with a compound of general formula (IV)

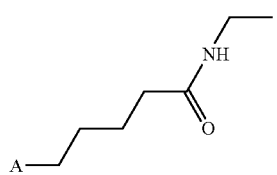

wherein A- represents a group selected from

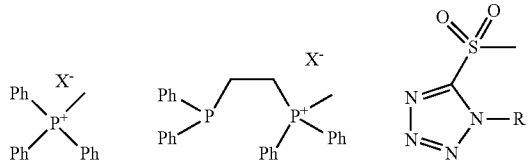

X represents a halide, and
R represents a C6 to C10 aryl or C1 or C10 alkyl residue, to give crude bimatoprost.

According to a further embodiment, the present invention relates to a process for the preparation of crude bimatoprost comprising at least step (x) and (y)

(x) reaction of a compound of formula (6)

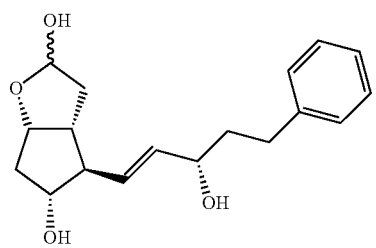

with a compound of general formula (V)

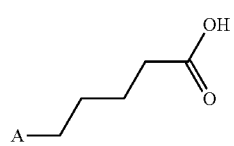

wherein A- represents a group selected from

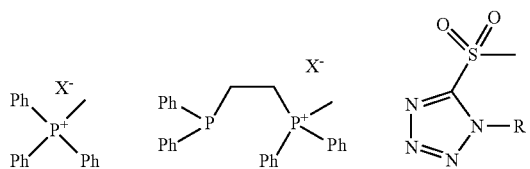

X represents a halide, and
R represents a C6 to C10 aryl or C1 or C10 alkyl residue, to give a compound of formula (7)

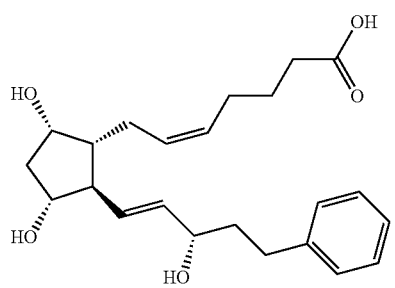

and
(y) conversion of the compound of formula (7) obtained in step (x) to give crude bimatoprost by activation of the carboxylic group of compound (7) as a mixed anhydride, and reaction of the activated intermediate with ethylamine.

According to the process of the present invention, pure bimatoprost can be obtained in an improved process.

DETAILED DESCRIPTION OF THE INVENTION

Figure 1:
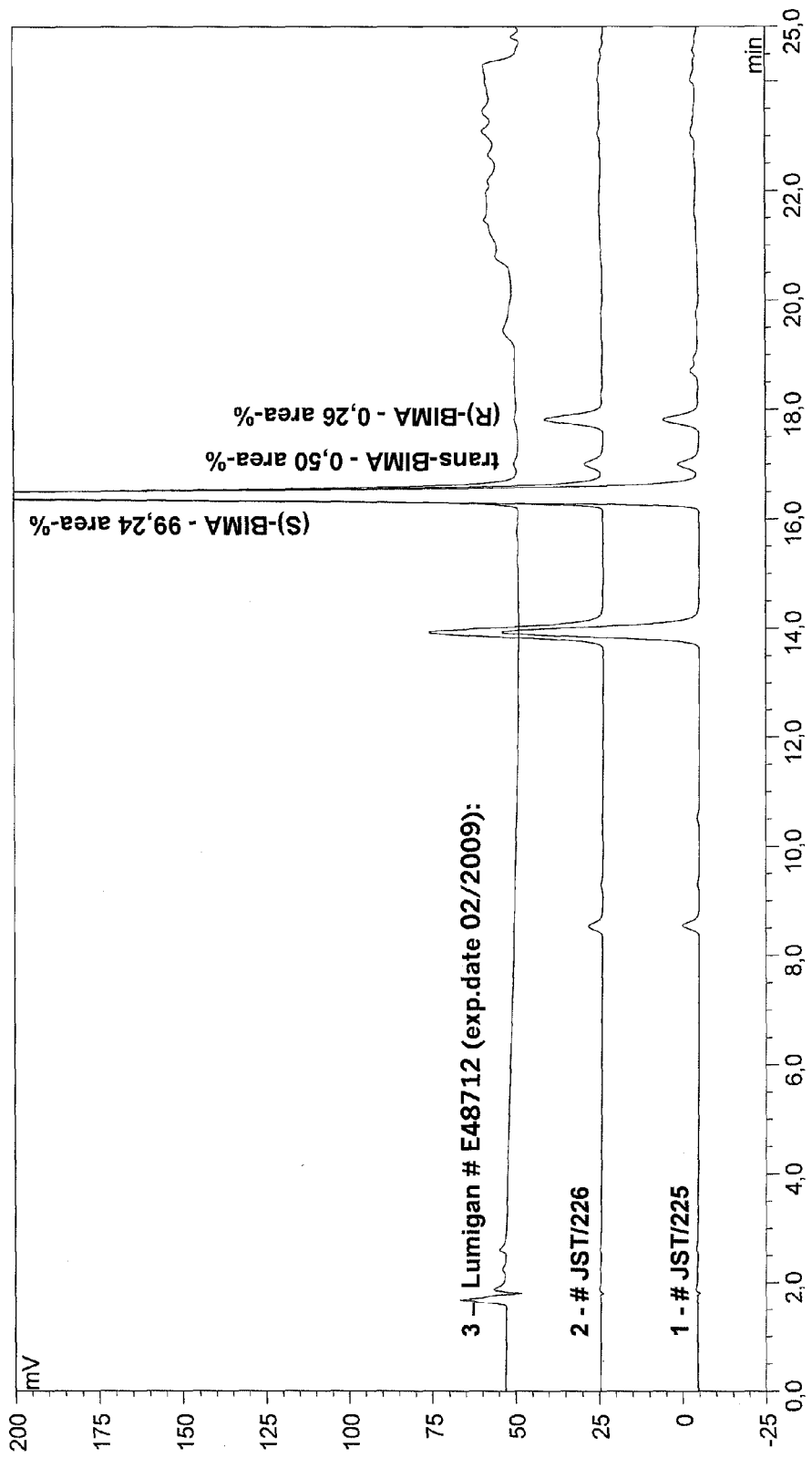
FIG. 1: shows a Chromatogram with
1) bimatoprost crude obtained using the described process;
2) bimatoprost crude obtained using the described process;
3) commercial sample of bimatoprost (Lumigan®).

The present invention relates to a process for the purification of crude bimatoprost comprising at least the steps of
(a) chromatography and
(b) crystallization of the product obtained in step (a).

In the context of the present invention, the term "crude bimatoprost" denotes a composition comprising bimatoprost and the impurities 15R-bimatoprost (29) and 5,6-trans-bimatoprost (30), respectively in an amount of more than 0.7% in total of any combination of 15R-bimatoprost (29) and 5,6-trans-bimatoprost (30), based on the weight of bimatoprost. The amount refers to the sum of 15R-bimatoprost (29) and 5,6-trans-bimatoprost (30). 15R-bimatoprost (29) and 5,6-trans-bimatoprost (30) are found as impurities in bimatoprost which is prepared according to any of the prior art processes and which is available on the market (e.g. Lumigan® which is an ophthalmic solution suitable to reduce increased eye pressure in patients suffering from open-angle glaucoma and ocular hypertension).

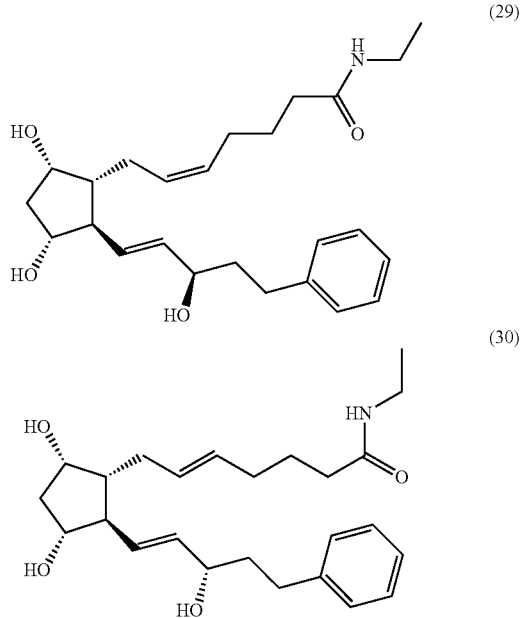

The level of side products can be decreased by e.g. recrystallisation of crude bimatoprost. However, even if the product is recrystallised several times the levels of compound (29) and (30) in total are always still above 0.7%.

In the context of the present invention, the term "pure bimatoprost" denotes a composition comprising bimatoprost and the impurities 15R-bimatoprost (29) and 5,6-trans-bimatoprost (30), respectively in an amount of less than 0.7% in total, for example from 0.01% to 0.7% in total, of any combination of 15R-bimatoprost (29) and 5,6-trans-bimatoprost (30), preferably less than 0.5% in total, for example from 0.01% to 0.5% in total, most preferably less than 0.2% in total, for example from 0.01% to 0.2% in total, based on the weight of bimatoprost.

It was now found that the two impurities 15R-bimatoprost (29) and 5,6-trans-bimatoprost (30) can be removed by the process according to the present invention to a level below 0.7% in total, for example from 0.01% to 0.7 in total, of any combination of 15R-bimatoprost (29) and 5,6-trans-bimatoprost (30), preferably below 0.5% in total, for example from 0.01% to 0.5% in total, most preferably below 0.2% in total, for example from 0.01% to 0.2% in total, by a combination of chromatography, in particular on an achiral stationary phase using an alcohol and an apolar solvent as eluent, and one crystallisation step.

By using the above separation procedures, it has been found possible to produce bimatoprost having a purity of greater than 99.3%, in particular greater than 99.5%, more particular of more than 99.8%.

Moreover, by using the above separation procedures, it has been found possible to produce bimatoprost that is substantially free of 15R-bimatoprost (29) and 5,6-trans-bimatoprost (30). As used herein, the phrase "substantially free of 15R-bimatoprost (29) and 5,6-trans-bimatoprost (30)" means that a composition comprising bimatoprost is of such high purity and high quality that most common side effects of ophthalmic solutions such as eye redness, itchy eyes, darkening of eye color, eyelash changes etc. are minimized.

Therefore, according to a further embodiment, the present invention also relates to bimatoprost having a purity of greater than 99.3%, in particular greater than 99.5%, more particular of more than 99.8%.

The process according to the present invention comprises at least two steps. According to step (a), a chromatography is performed. This can be done using an achiral stationary phase and an eluent comprising an alcohol and an apolar solvent. The product obtained in step (a) is further treated in step (b). According to step (b), crystallisation of the product obtained in (a) is performed to obtain pure bimatoprost.

The process of the present invention can also comprise further steps before step (a) or after step (b), for example an extraction step or a further crystallisation step.

According to the present invention, crude bimatoprost is purified.

According to a preferred embodiment, the present invention relates to a process for the purification of crude bimatoprost as disclosed above, wherein the chromatography is carried out using an achiral stationary phase and an eluent comprising an alcohol and an apolar solvent.

Preferably, a chromatographic system is used in step (a) which is based on the use of silica as stationary phase and on an alcohol in combination with an apolar solvent as eluent.

Therefore, according to a further embodiment, the present invention also relates to a process for the purification of crude bimatoprost as disclosed above, wherein the stationary phase comprises silica.

The eluent used comprises an alcohol, such as methanol or ethanol, and an apolar coeluent, such as heptane, hexane, or cyclohexane.

Therefore, according to a further embodiment, the present invention also relates to a process for the purification of crude bimatoprost as disclosed above, wherein the alcohol is selected from methanol and ethanol and the apolar solvent is selected from heptane, hexane and cylcohexane.

Preferably, the alcohol and the apolar solvent are used in a ratio of 85:15 to 97:3.

In a preferred embodiment, heptane and ethanol are used as eluent. More preferably, heptane and ethanol in a ratio of 94:6 to 96:4 are used as eluent.

Conditions for the chromatography according to step (a) are known to the person skilled in the art.

The chromatographic purification is followed by a crystallisation of bimatoprost according to step (b). In principle, all suitable methods for crystallisation can be used for the process of the present invention.

The crystallisation can in particular be performed from ethers such as MTBE or diethylether, acetonitrile, alcohols, esters, such as isopropyl acetate, or mixtures of any of these solvents. In a preferred embodiment the crystallisation is performed in acetonitrile or MTBE or mixtures of these two solvents.

Therefore, according to a further embodiment, the present invention also relates to a process for the purification of crude bimatoprost as disclosed above, wherein the crystallisation is performed from a solvent selected from ethers, acetonitrile, alcohols, esters, or mixtures of any of these solvents.

The combination of chromatographic purification and crystallisation gives bimatoprost of high purity with a level of by-products (29) and (30) below 0.7% in total, for example from 0.01% to 0.7% in total, preferably below 0.5% in total, for example from 0.01% to 0.5% in total, most preferably below 0.2% in total, for example from 0.01% to 0.2% in total.

According to a further embodiment, the present invention also relates to bimatoprost substantially free of 15R-bimatoprost and 5,6-trans-bimatoprost.

According to one embodiment, the present invention also relates to bimatoprost containing less than 0.7% in total, for example from 0.01% to 0.7% in total, of any combination of 15R-bimatoprost and 5,6-trans-bimatoprost.

According to one embodiment, the present invention also relates to bimatoprost containing less than 0.5% in total, for example from 0.01% to 0.5% in total, of any combination of 15R-bimatoprost and 5,6-trans-bimatoprost.

According to one embodiment, the present invention also relates to bimatoprost containing less than 0.2% in total, for example from 0.01% to 0.2% in total, of any combination of 15R-bimatoprost and 5,6-trans-bimatoprost.

According to the present invention, crude bimatoprost which is purified according to the process of the present invention can be obtained according to any process known to the person skilled in the art.

After the reaction and prior to the purification, crude bimatoprost can be isolated by an aqueous work-up consisting of extractions with aqueous acids and bases in combination with a solvent which can dissolve bimatoprost. In a preferred embodiment $CH_2Cl_2$, methyl tert-butylether, or toluene are used for this purpose. Preferably, crude bimatoprost is obtained after removal of the solvent.

Crude bimatoprost as obtained by a process according to the state of the art, generally contains about 2% of 5,6-trans-bimatoprost (30) and variable amounts of 15R-bimatoprost (29). The level of the latter by-product depends on the level of the corresponding 15R isomer in the starting material. If the compound is prepared according to EP 0 364 417 A1 using the reduction described in U.S. Pat. No. 5,698,733 the level of the corresponding 15R isomer in the starting material is usually 4 to 6%. Crude bimatoprost, prepared from such a starting material using one of the processes described above, usually contains about 3 to 5% of compound (29).

The quality of crude bimatoprost can be improved by several crystallization steps to give bimatoprost which contains the impurities 15R-bimatoprost (29) and 5,6-trans-bimatoprost (30), respectively, in an amount of still at least 0.7%, based on the weight of bimatoprost.

According to the present invention, crude bimatoprost is preferably prepared by a simple and efficient process which allows for a simple and efficient overall process. Preferably, crude bimatoprost is prepared by a process using only few protection groups to simplify the process.

It has been found that the compound of formula (6) can be directly converted to crude bimatoprost without using protection groups by a reaction with a compound of general formula (IV).

Therefore, according to a further embodiment, the present invention also relates to a process for the preparation of crude bimatoprost comprising at least step (i)

(i) reaction of a compound of formula (6)

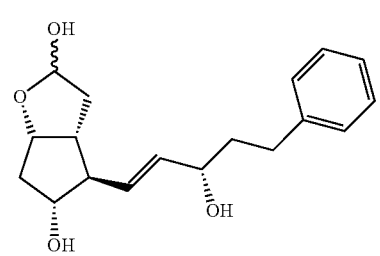

6 with a compound of general formula (IV)

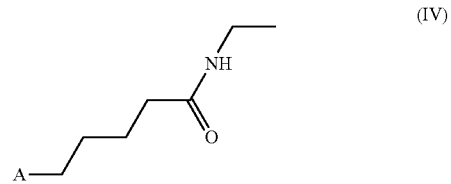

(IV)

wherein A- represents a group selected from

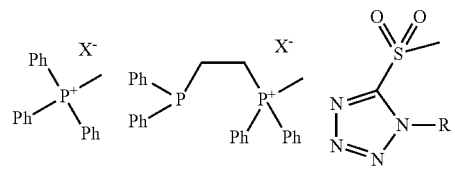

X represents a halide, and

R represents a C6 to C10 aryl or C1 or C10 alkyl residue, to give crude bimatoprost.

According to the present invention, hemiacetal (6) serves as starting material for the reaction according to step (i). This compound of formula (6) can be prepared as described in EP 0 364 417 A1 and using the reduction as described in U.S. Pat. No. 5,698,733.

According to step (i), the compound of formula (6) is reacted with a compound of general formula (IV). Any suitable reaction conditions known to the person skilled in the art can be applied for the reaction according to step (i).

The compound of general formula (IV) used in step (i) is a compound selected from compounds of formula (23), (27) or (28)

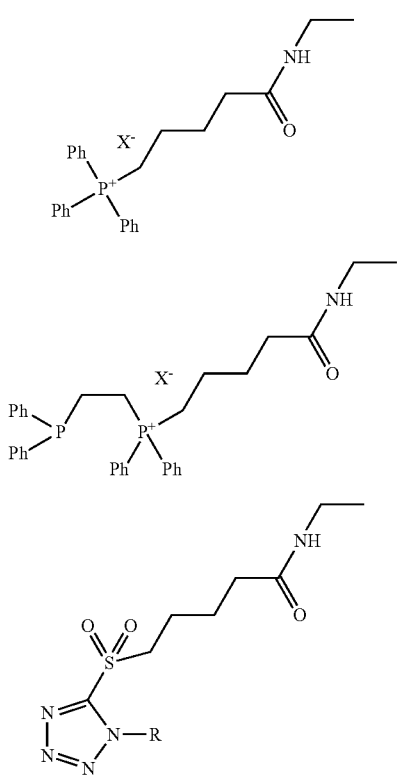

wherein X represents a halide, and R represents a C6 to C10 aryl or C1 or C10 alkyl residue.

According to a preferred embodiment, the compound of general formula (IV) used in step (i) is a compound of formula (23).

According to a preferred embodiment, the compound of formula (6) is reacted with a compound of formula (23), (27), or (28) in the presence of a suitable base, such as alkali or alkaline earth metal alkoxides, hydroxides, carbonates, or oxides, sodium, potassium, or lithium hexamethylsilazide, tetramethylguanidine, or 1,8-diazabicyclo[5.4.0]undec-7-en (DBU) to directly give crude bimatoprost.

It is important to note that step (i) can be carried out without the use of protecting groups, which is an improvement in comparison to the prior art (WO 2003/074481).

Preferably, according to step (i), the compound of the formula (6) is subjected to a Wittig reaction with an ylide, the ylide being formed by reaction of a compound of the formulas (23), (27), or (28) with a base, wherein X represents a halogen and R represents $C_{1-6}$ alkyl or $C_{6-10}$ aryl. Preferred bases for the formation of the yilde include alkali or alkaline earth metal alkoxides, such as sodium ethoxide, potassium ethoxide, or potassium tert-butoxide, alkali or alkaline earth metal hydroxides, carbonates, or oxides, sodium, potassium, or lithium hexamethylsilazide, tetramethylguanidine, or 1,8-diazabicyclo[5.4.0]undec-7-en (DBU), organolithium reagents including butyllithium, hexyllithium, and heptyllithium, metal amides such as sodium amide, metal hydrides such as sodium hydride. More preferred bases are alkali metal alkoxides, and most preferably potassium tert-butoxide is used.

It is preferred to run the reaction according to step (i) in an inert aprotic organic solvent including toluene, hexane, heptane, THF, MTBE, or mixtures thereof. Most preferably, THF is used.

In one preferred embodiment the compound of formula (IV), in particular the compound (23), is used for the process and 3.0 to 15.0 equivalents of the compound of formula (IV), in particular halide (23) relative to the amount of compound (6), more preferably, 5.0 to 10.0 equivalents are used.

It is further preferred to use 3.0 to 30.0 equivalents of base relative to the amount of compounds of the formula (6), more preferably, 5.0 to 15.0 equivalents are used.

It is preferred to run the reaction according to step (i) at −20° C.-20° C.

According to the present invention, it is also possible to prepare crude bimatoprost by reaction of a compound of formula (6) with a compound of general formula (V)

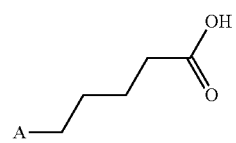

to give a compound of formula (7) and subsequent formation of crude bimatoprost.

Therefore, according to a further embodiment, the present invention also relates to a process for the preparation of crude bimatoprost comprising at least step (x) and (y)

(x) reaction of a compound of formula (6)

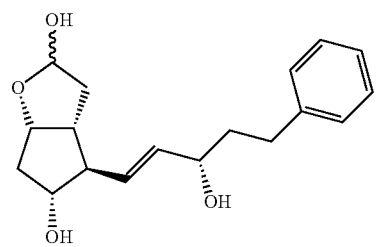

with a compound of general formula (V)

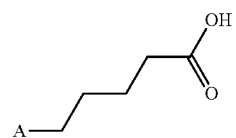

wherein A- represents a group selected from

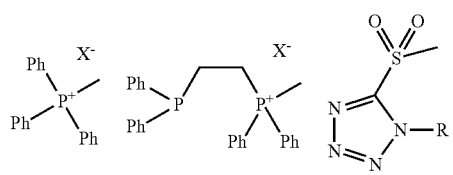

X represents a halide, and
R represents a C6 to C10 aryl or C1 or C10 alkyl residue, to give a compound of formula (7)

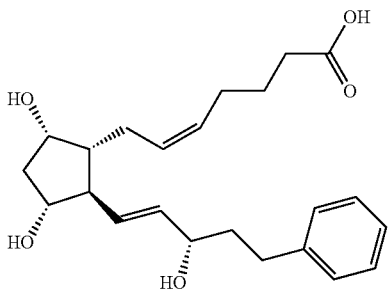

and (y) conversion of the compound of formula (7) obtained in step (x) to give crude bimatoprost by activation of the carboxylic group of compound (7) as a mixed anhydride, and reaction of the activated intermediate with ethylamine.

According to step (x), the compound of formula (6) is reacted with a compound of general formula (V). Any suitable reaction conditions known to the person skilled in the art can be applied for the reaction according to step (x).

The compound of general formula (V) used in step (x) is a compound selected from compounds of formula (24), (25) or (26)

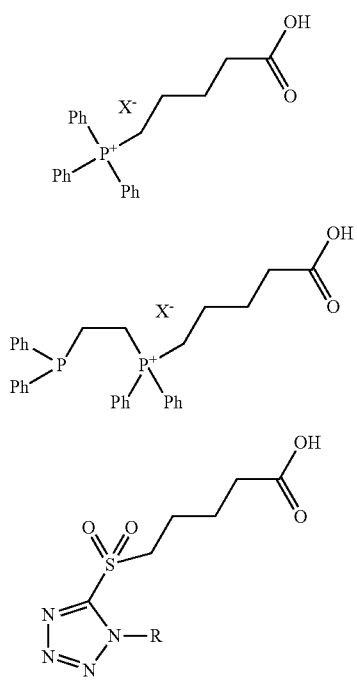

wherein X represents a halide, and R represents a C6 to C10 aryl or C1 or C10 alkyl residue.

According to a preferred embodiment, the compound of general formula (V) used in step (x) is a compound of formula (24).

Said process according to step (x) comprises subjecting compounds of the formula (6) to a Wittig reaction with an ylide, the ylide being formed by reaction of a compound of the formulas (24), (25), or (26) with a base, wherein X represents a halogen and R represents $C_{1-6}$ alkyl or $C_{6-10}$ aryl. Preferred bases for the formation of the yilde include alkali or alkaline earth metal alkoxides, such as sodium ethoxide, potassium ethoxide, or potassium tert-butoxide, alkali or alkaline earth metal hydroxides, carbonates, or oxides, sodium, potassium, or lithium hexamethylsilazide, tetramethylguanidine, or 1,8-diazabicyclo[5.4.0]undec-7-en (DBU), organolithium reagents including butyllithium, hexyllithium, and heptyllithium, metal amides such as sodium amide, metal hydrides such as sodium hydride. More preferred bases are alkali metal alkoxides, and most preferably potassium tert-butoxide is used. It is preferred to run the reaction in an inert aprotic organic solvent including toluene, hexane, heptane, THF, MTBE, or mixtures thereof. Most preferably, THF is used.

In one preferred embodiment the compound of formula (V), in particular the compound (24) is used for the process and 3.0 to 15.0 equivalents of the compound of formula (V), in particular of halide (24) relative to the amount of compound (6), more preferably, 5.0 to 10.0 equivalents are used. It is further preferred to use 3.0 to 30.0 equivalents of base relative to the amount of compounds of the formula (6), more preferably, 5.0 to 15.0 equivalents are used.

It is preferred to run the reaction according to step (x) at −20° C. to 20° C.

The compound of the formula (7) can be isolated and purified by methods know to a person skilled in the art but it is preferred not to isolate the compound of formula (7) but use it in solution as obtained after work-up for the next step. Preferably compound (7) is used as a solution.

An advantage of using compounds (25) and (26) as ylide precursors is that the reagent derived by-products can be readily removed by aqueous washings.

Therefore, according to a further embodiment, the present invention also relates to a process for the preparation of crude bimatoprost as disclosed above, wherein the reaction according to step (i) or according to step (x) is performed in the presence of a base selected from alkali or alkaline earth metal alkoxides, alkali or alkaline earth metal hydroxides, carbonates, or oxides, sodium, potassium, or lithium hexamethylsilazide, tetramethylguanidine, or 1,8-diazabicyclo[5.4.0]undec-7-en (DBU), organolithium reagents, metal amides, or metal hydrides.

According to step (y), the compound of formula (7) obtained in step (x) is reacted to give crude bimatoprost by activation of the carboxylic group of compound (7) as a mixed anhydride, and reaction of the activated intermediate with ethylamine.

Said process comprises forming a mixed anhydride with an organic or inorganic acid and the carboxylic function of compound (7) and subjecting the mixed anhydrides to a reaction with ethylamine to obtain crude bimatoprost. Suitable reagents for the formation of mixed anhydrides include carboxylic acid chlorides such as pivalic acid chloride, chloroformates such as $C_{1-6}$ alkyl chloroformate, or dialkylphosphinyl chlorides. Preferably, pivalic acid chloride or $C_{1-6}$ alkyl chloroformate are used.

Therefore, according to a further embodiment, the present invention also relates to a process for the preparation of crude bimatoprost as disclosed above, wherein in step (y), activation of the carboxylic group is achieved by reaction with pivalic acid chloride or chloroalkylformate in the presence of a base.

The formation of the mixed anhydrides is generally performed in the presence of a base. Preferred bases are tertiary amines, such as triethylamine or diisopropylethylamine.

The reaction is generally performed in an organic solvent with 0.9 to 2.0 equivalents of activating agent, more preferably with 1.0 to 1.2 equivalents. It is preferred to further process the mixed anhydride in situ without isolation. The conversion of the mixed anhydride to crude bimatoprost is preferably performed by adding 1.0 to 10.0 equivalents of ethylamine.

According to a further embodiment, the present invention also relates to a process for preparing pure bimatoprost comprising the steps (i), (a), and (b) or a process comprising the steps (x), (y), (a), and (b). The process for preparing pure bimatoprost according to the present invention can also comprise further steps. With respect to the individual steps and preferred embodiments, reference is made to the above disclosure.

The major advantage of the described process is that the reaction times are significantly shortened as compared to prior art processes which are based on the conversion of acid (7) into the corresponding methyl ester which is further converted to crude bimatoprost in a slow reaction with reaction times of more than 48 h.

The present invention allows the conversion of acid (7) into bimatoprost crude in less than 10 h.

The combination of chromatographic purification and crystallisation gives bimatoprost of high purity with a level of by-products (29) and (30) below 0.2%, in particular below 0.1%.

Figure 2:
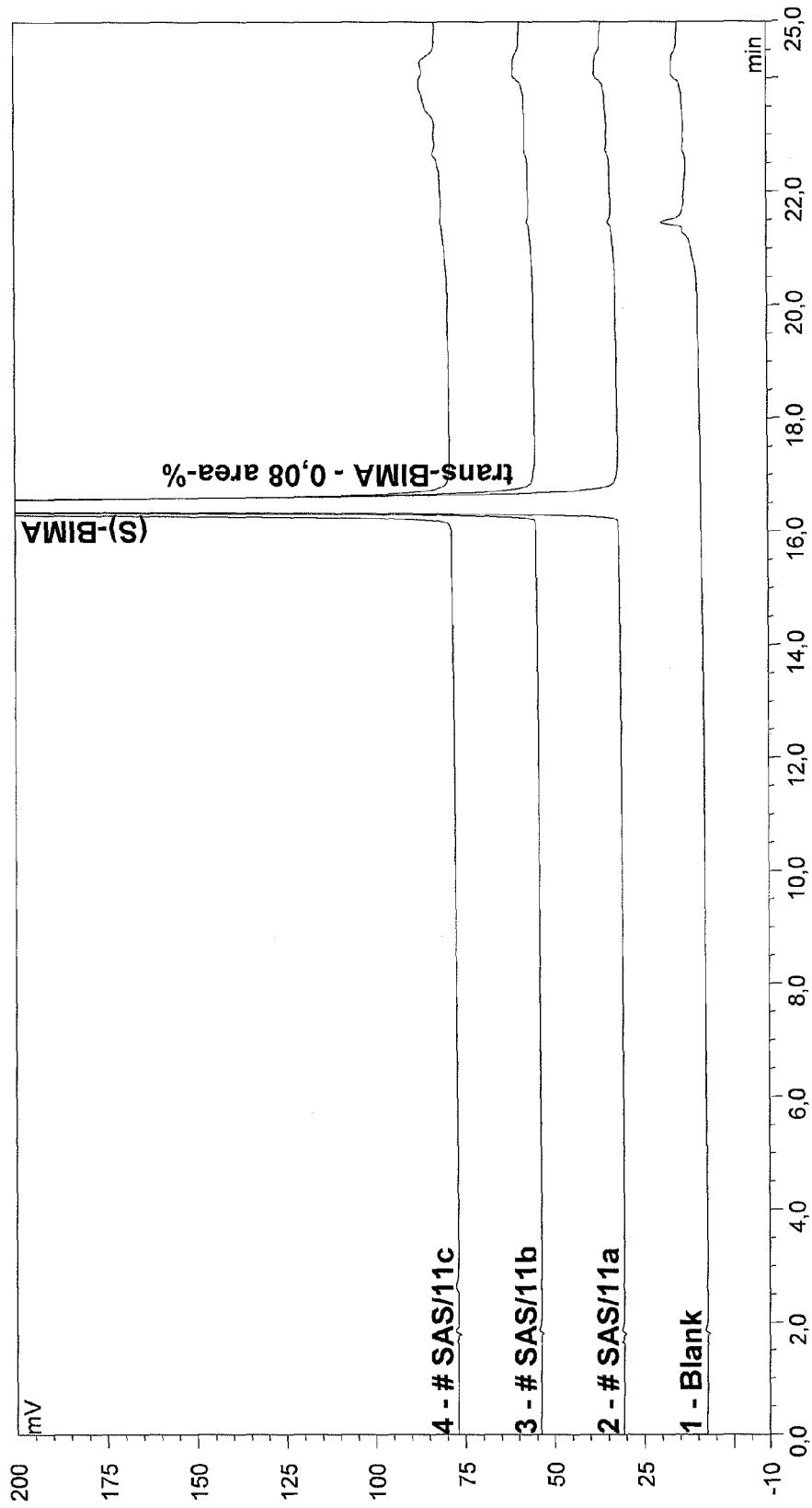
FIG. 2: shows a Chromatogram with 1) blank and 2)-4) bimatoprost pure as obtained by using the described process.

In FIGS. 1 and 2 chromatograms of a commercial sample of bimatoprost and bimatoprost crude and bimatoprost pure prepared according to the present invention are depicted.

Unless otherwise noted, all %-values in the present application are given as % by weight.

EXAMPLES

The following examples describe the present invention in detail, but they are not to be construed to be in any way limiting for the present invention.

All examples were carried out under an atmosphere of nitrogen if necessary.

Example 1

Bimatoprost

Synthesis of Compound (7) from Compound (6)

a)

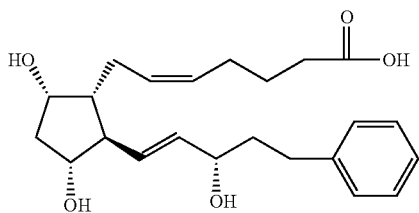 [SMILES: O=C(O)CCC/C=C\C[C@@H]1[C@@H](/C=C/[C@@H](O)CCc2ccccc2)[C@H](O)C[C@@H]1O]

A suspension of 33.1 g of (4-carboxybutyl)triphenylphosphonium bromide (MW=443.32; 7.5 equivalents) in 95 mL of THF was cooled to 0° C. At this temperature 139.4 g of a 2M solution of potassium-tert butoxide (MW=112.21; 9.5 equivalents) in THF were added drop wise over 30 min and stirring was continued at 0° C. for 30 min. The resulting orange red suspension was cooled to a mass temperature of −17° C. To the red ylide containing suspension a solution of 8 g of (3αR,4R,5R,6αS)-4-((R)-3-hydroxy-5-phenyl-pentyl)-hexahydro-cyclopenta[b]furan-2,5-diol (compound (6), MW=304.39; 1 equivalents) dissolved in 24 mL of THF was added over 30 min and the reaction mixture was stirred at −17° C. until complete conversion was detected. Then, 180 mL of brine were added to the slight orange cold suspension. The resulting decolorized suspension was stirred for 30 min at ≥−10° C. Then, the suspension was filtered over a G3 suction funnel and washed with 20 mL of brine. The combined filtrates were washed two times with 180 mL of toluene. 180 mL of MTBE were added to the aqueous layer and the pH was adjusted to 2.0-1.5 by addition of approx. 20 g of 20% aqueous sulfamic acid. After stirring for 5 min the layers were separated. The aqueous layer was extracted once more with 180 mL of MTBE. The MTBE layers were combined and washed with 180 mL of brine. The organic layer was concentrated at 45° C. and 200 mbar to a volume of 100 mL. To the concentrate 50 g of DMF were added and MTBE was removed under reduced pressure (100 mbar) at 45° C. to a final mass of 65 g. The resulting solution of compound (7) in DMF was used in the next step without further purification.

Synthesis of Bimatoprost from Compound (7)

Comparison Example: Synthesis Via Methylester of (7)

b)

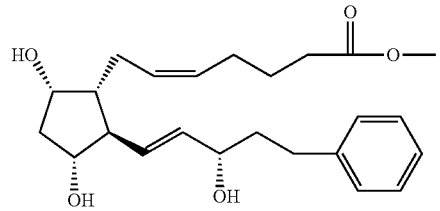 [SMILES: COC(=O)CCC/C=C\C[C@@H]1[C@@H](/C=C/[C@@H](O)CCc2ccccc2)[C@H](O)C[C@@H]1O]

To the solution of (Z)-7-[(1R,2R,3R,5S)-3,5-dihydroxy-2-((R)-3-hydroxy-5-phenyl-pent-1-enyl)-cyclopentyl]-hept-5-enoic acid (7) in DMF (preparation see above) 5.8 g (MW=388.51; 1 equivalents) of powdered potassium carbonate (MW=138.21; 1.6 equivalents) were added. After stirring the suspension for 15 min at ambient temperature, 6.6 g of methyliodide (MW=141.94; 1.5 equivalents) were added. Then the mixture was heated to 50° C. and stirred for 18 h at 50° C. After complete conversion the reaction mixture was diluted with 390 mL of MTBE and 125 mL of water and the pH was adjusted by addition of 20% aqueous sulfamic acid to 2.0-1.5. After stirring for 5 min the layers were separated. The aqueous layer was discarded. Die MTBE layer was washed three times with 50 mL of water and then with 125 mL of 8.6% aqueous sodium carbonate. Finally the organic layer was washed two times with 125 mL of water at a pH of 6.5 which is adjusted by addition of 15% aqueous citric acid. The combined MTBE layers were concentrated at 45° C. and 100 mbar to yield in 8.08 g of crude (Z)-7-[(1R,2R,3R,5S)-3,5-dihydroxy-2-((R)-3-hydroxy-5-phenyl-pent-1-enyl)-cyclopentyl]-hept-5-enoic acid methylester. The resulting oil was used in the next step without further purification.

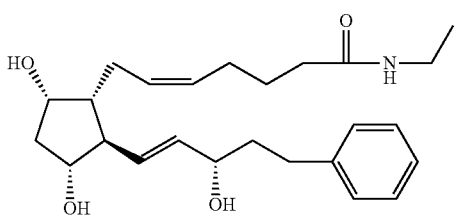 [SMILES: CCNC(=O)CCC/C=C\C[C@@H]1[C@@H](/C=C/[C@@H](O)CCc2ccccc2)[C@H](O)C[C@@H]1O]

56 g of ethylamine (MW=45.08; 47.9 equivalents) in 24 mL of water were added to 8.08 g of crude (Z)-7 [(1R,2R,3R,5S)-3,5-dihydroxy-2-((R)-3-hydroxy-5-phenyl-pent-1-enyl)-cyclo-pentyl]hept-5-enoic acid methylester (MW=402.54; 1 equivalents) and the resulting solution was stirred for 48 h at 23° C. The excess of ethylamine was removed by distillation in vacuo (25°, 100 mbar) after complete conversion. To the residue were added 400 mL of methylenechloride and 100 mL of water and the pH was adjusted to 1.5 by addition of 1M aqueous hydrochloric acid. After separation of the layers the organic layers were washed with 100 mL of saturated aqueous sodium bicarbonate, 100 mL of water, and 100 mL of brine. The solution was filtered and concentrated in vacuo yielding 8.33 g of oily bimatoprost crude. To the residue were added 25 mL of acetonitrile. After adding seeds the mixture was stirred for 30 minutes at ambient temperature, cooled to 0° C. and stirred for two hours at this temperature.

The crystal suspension was cooled to −20° C. After stirring for 14 hours at −20° C. the crystals were isolated by filtration, washed with cold acetonitrile and then dried in vacuo yielding 5.47 g crystalline bimatoprost (mp 70-74° C.).

Example 2

Bimatoprost (Via Mixed Anhydride with Pivalic Acid)

Synthesis of Compound (7) from Compound (6)

a)

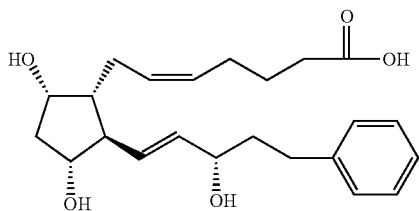 [SMILES: O=C(O)CCC/C=C\C[C@@H]1[C@@H](/C=C/[C@@H](O)CCc2ccccc2)[C@H](O)C[C@@H]1O]

A suspension of 33.1 g of (4-carboxybutyl)triphenylphosphonium bromide (MW=443.32; 7.5 equivalents) in 95 mL of THF was cooled to 0° C. At this temperature 139.4 g of a 2M solution of potassium-tert butoxide (MW=112.21; 9.5 equivalents) in THF were added drop wise over 30 min and stirring was continued at 0° C. for 30 min. The resulting orange red suspension was cooled to a mass temperature of −17° C. To the red ylide containing suspension a solution of 8 g of (3αR,4R,5R,6αS)-4-((R)-3-hydroxy-5-phenyl-pentyl)-hexahydro-cyclopenta[b]furan-2,5-diol (compound (6), MW=304.39; 1 equivalents) dissolved in 24 mL of THF was added over 30 min and the reaction mixture was stirred at −17° C. until complete conversion was detected. Then, 180 mL of brine were added to the slight orange cold suspension. The resulting decolorized suspension was stirred for 30 min at ≤−10° C. Then, the suspension was filtered over a G3 suction funnel and washed with 20 mL of brine. The combined filtrates were washed two times with 180 mL of toluene. 180 mL of MTBE were added to the aqueous layer and the pH was adjusted to 2.0-1.5 by addition of approx. 20 g of 20% aqueous sulfamic acid. After stirring for 5 min the layers were separated. The aqueous layer was extracted once more with 180 mL of MTBE. The MTBE layers were combined and washed with 180 mL of brine. The organic layer was concentrated at 45° C. and 100 mbar to give 12.34 g of bimatoprost acid (7) (MW=402.54), which was used in the next step without further purification.

b)

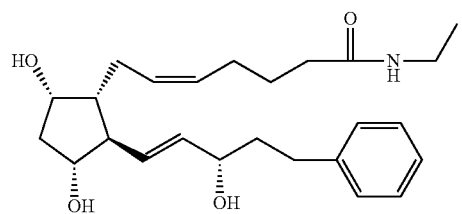 [SMILES: CCNC(=O)CCC/C=C\C[C@@H]1[C@@H](/C=C/[C@@H](O)CCc2ccccc2)[C@H](O)C[C@@H]1O]

Under an atmosphere of nitrogen 250 mL methylenechloride were added to 12.34 g of (Z)-7-[(1R,2R,3R,5S)-3,5-dihydroxy-2-((R)-3-hydroxy-5-phenyl-pent-1-enyl)-cyclopentyl]-hept-5-enoic acid (compound (7), MW=402.54; 26.1 mmol; 1 equivalents) and the solution was cooled to −10° C. At this temperature 5.1 g of triethylamine (MW=101.19; 50.4 mmol; 1.9 equivalents) and 5.8 g of pivalic acid chloride (MW=120.58; 48.1 mmol; 1.8 equivalents) were added. The reaction mixture was stirred for two hours. Then a solution of 2.3 g ethylamine (MW=45.08; 2.0 equivalents) in 10 mL of methylene chloride was added. After stirring the reaction mixture for two hours at −10° C., the mixture was warmed to room temperature. The reaction was quenched by adding 250 mL of water and adjusting the pH to 2.0 with 1M aqueous hydrochloric acid. After separation of the layers, the organic layers was washed with 250 mL of saturated aqueous sodium bicarbonate, water and brine. After filtration the solution was concentrated under reduced pressure to give 18.4 g of bimatoprost crude (yield: 95%; as determined by NMR). Bimatoprost crude was purified as described below.

Example 3

Bimatoprost (Via Mixed Anhydride with Ethyl Chloroformate)

a) 12.3 g of compound (7) were prepared as described in example 2a.

b)

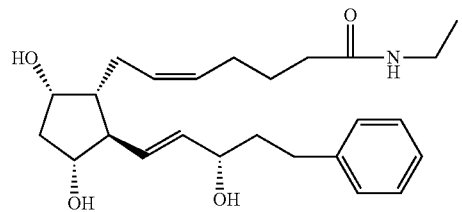 [SMILES: CCNC(=O)CCC/C=C\C[C@@H]1[C@@H](/C=C/[C@@H](O)CCc2ccccc2)[C@H](O)C[C@@H]1O]

250 mL of methylene chloride were added to 12.3 g of (Z)-7-[(1R,2R,3R,5S)-3,5-dihydroxy-2-((R)-3-hydroxy-5-phenyl-pent-1-enyl)-cyclopentyl]-hept-5-enoic acid (compound (7), MW=402.54; 26.1 mmol; 1 equivalents). The solution is cooled to −10° C. At this temperature 5.1 g of triethylamine (MW=101.19; 50.4 mmol; 1.9 equivalents) and 5.1 g of ethyl chloroformate (MW=108.52; 48.1 mmol; 1.8 equivalents) were added and the mixture was stirred for two hours. A solution of 2.3 g of ethylamine (MW=45.08; 2.0 equivalents) in 10 mL methylenehloride was added. After stirring the reaction mixture for two hours at −10° C., the mixture was warmed to room temperature. The reaction was quenched by addition of 250 mL of water and the pH is adjusted to 2.0 with 1M aqueous hydrochloric acid. After separation of the layers, the organic layer was washed with 250 mL of saturated aqueous sodium bicarbonate, water and brine. After filtration the solution was concentrated under reduced pressure to give 13.1 g of bimatoprost crude (yield: 89%; as determined by NMR). Bimatoprost crude was purified as described below.

Example 4

Bimatoprost (Via 4-ethylcarbamoyl-butyl)triphenylphosphonium bromide)

a) A suspension of 15.0 g of (4-ethylcarbamoyl-butyl)triphenylphosphonium bromide (MW=470.39; 3.2 equivalents) in 50 mL of THF was cooled to 0° C. At this temperature 11.9 g of a 2M solution of potassium-tert butoxide (MW=112.21; 3.3 equivalents) in THF were added drop wise over 30 min and stirring was continued at 0° C. for 30 min. The resulting orange red suspension was cooled to a mass temperature of −17° C. To the red suspension of the ylide a solution of 3.57 g of (3αR,4R,5R,6αS)-4-((R)-3-hydroxy-5-phenyl-pent-1-enyl)-hexahydro-cyclopenta[b]furan-2,5-diol (compound (6), MW=306.41; 1 equivalents) in 24 mL of THF was added over 30 min and the reaction mixture was stirred at −17° C. for about 20 h. To the slightly orange suspension 180 mL of brine and 80 mL of MTBE were added and the pH was adjusted to 2.0 by stirring of 20% aqueous sulfamic acid. After stirring for 5 min the layers were separated. The aqueous layer was extracted once with 80 mL of MTBE. The MTBE layers were combined and washed with 80 mL of brine and the pH was adjusted to 7.5 by addition of saturated aqueous sodium bicarbonate. The filtered organic layer was concentrated at 45° C. and 100 mbar to give 15.0 g of crude bimatoprost (yield ~80% as estimated by NMR), which was purified as described below.

Example 5

Purification of Bimatoprost by Silica Gel Chromatography and Crystallisation

Bimatoprost crude, as obtained by examples 2, 3, and 4 contained 4-5% of 15R-bimatoprost (29) and 2-3% of 5,6-trans-bimatoprost (30) relative to bimatoprost. The remaining impurities were Wittig reagent derived compounds. The assay of bimatoprost in the individual bimatoprost crude samples was in the range of 30% to 90%.
a) Chromatography 10 g of bimatoprost crude (as obtained in example 3b) were dissolved in 50 mL of heptane/EtOH 1/1. The crude product was purified on a preparative HPLC system using silica as stationary phase and heptane/EtOH 5/95 as eluent. 7 g of bimatoprost pure were obtained after evaporation of the solvent. The assay of bimatoprost after chromatography was 99.5% with impurity levels of <0.15%.

The above HPLC procedure is preferably carried out on a silica gel column. Examples of suitable columns include WatersRT" Spherisorb, Phenomenex® Luna Cyano and Phenomenex" Luna Silica or YMC-Pack-Silica.

b) Crystallisation

Bimatoprost as obtained in example 5a with an assay of 99.5% and impurity levels of <0.15% was further purified by crystallisation from acetonitrile or MTBE to give bimatoprost with 99.9% purity and impurity levels of <0.10%.

The purity of bimatoprost was determined using a Chiracel OD-RH 4.6×150 mm (5 μm) column.

Eluant A: 2.62 g sulfamic acid in 1000 g H$_2$O; eluant B: 40:60 H$_2$O/acetonitrile, flow rate 1.1 mL/min; 35° C.; 210 nm.

| Gradient: % B | 15% | 0 min |
|---|---|---|
| | 55% | 18 min |
| | 100% | 25 min |
| Retention times: | 16.4 min | bimatoprost |
| | 17.0 min | compound (30) |
| | 17.9 min | compound (29) |

This procedure allows detection levels of any combination of 15R-bimatoprost and 5,6-trans-bimatoprost down to 0.01% in total based on the weight of bimatoprost. Thus, using this procedure, it is possible to achieve bimatoprost that is substantially free of the hitherto difficult to remove impurities.

The invention claimed is:

1. A method for the purification of crude bimatoprost according to formula (I)

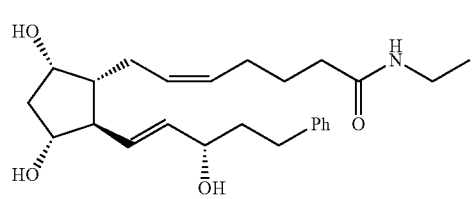

comprising at least the steps of:

(a) subjecting crude bimatoprost according to formula (I) to chromatography to form a product, wherein the chromatography is carried out using an achiral stationary phase comprising silica and an eluent comprising an alcohol and an apolar solvent, and wherein the alcohol is selected from methanol and ethanol and the apolar solvent is selected from heptane, hexane and cylcohexane; and (b) crystallizing the product obtained in step (a) from a solvent selected from ethers, acetonnitrile, alcohols, esters, or mixtures of any of these solvents to form pure bimatoprost containing less than 0.2% in total of any combination of 15R-bimatoprost and 5, 6-trans-bimatoprost.

2. The method according to claim 1, further comprising preparing the crude bimatoprost by (i) reacting a compound of formula (6)

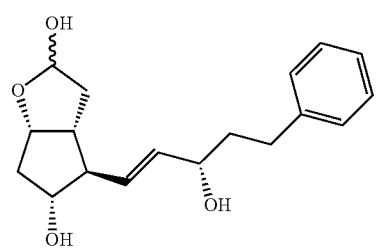

with a compound of general formula (IV)

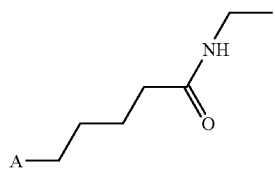

wherein A- represents a group selected from

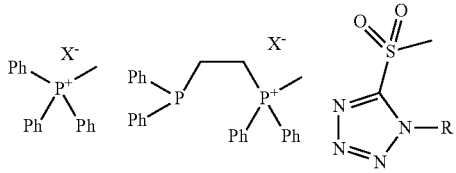

X represents a halide; and
R represents a C6 to C10 aryl or C1 or C10 alkyl residue, to provide the crude bimatoprost.

3. A method for the preparation of crude bimatoprost comprising at least step (i):

(i) reacting a compound of formula (6)

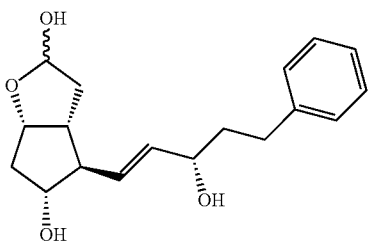

with a compound of general formula (IV)

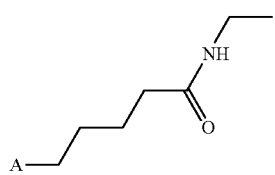

wherein A- represents a group selected from

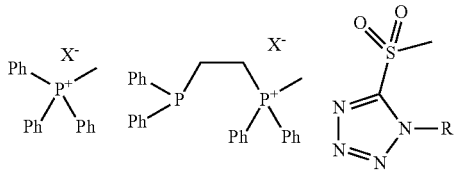

X represents a halide; and
R represents a C6 to C10 aryl or C1 or C10 alkyl residue, to provide crude bimatoprost.

4. The method according to claim 3, wherein the reaction according to step (i) is performed in the presence of a base selected from alkali or alkaline earth metal alkoxides, alkali or alkaline earth metal hydroxides, carbonates, or oxides, sodium, potassium, or lithium hexamethylsilazide, tetramethylguanidine, or 1,8-diazabicyclo[5.4.0]undec-7-en (DBU), organolithium reagents, metal amides, or metal hydrides.

5. A method for the preparation of crude bimatoprost comprising at least step (x) and (y):

(x) reacting a compound of formula (6)

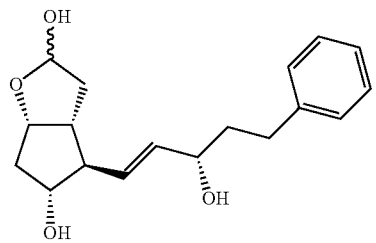

with a compound of general formula (V)

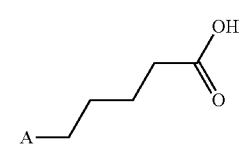

wherein A- represents a group selected from

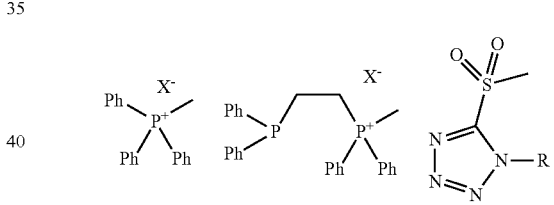

X represents a halide; and
R represents a C6 to C10 aryl or C1 or C10 alkyl residue, to provide a compound of formula (7)

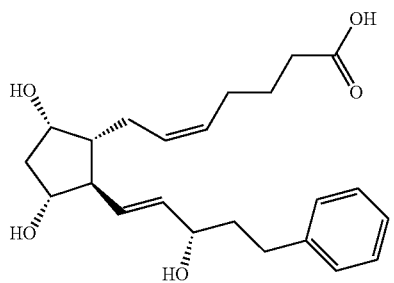

and
(y) converting the compound of formula (7) obtained in step (x) to provide crude bimatoprost by activation of the carboxylic group of compound (7) as a mixed anhydride to form an activated intermediate, and reacting the activated intermediate with ethylamine.

6. The method according to claim 5, wherein the reaction according to step (x) is performed in the presence of a base selected from alkali or alkaline earth metal alkoxides, alkali or alkaline earth metal hydroxides, carbonates, or oxides, sodium, potassium, or lithium hexamethylsilazide, tetramethylguanidine, or 1,8-diazabicyclo[5.4.0]undec-7-en (DBU), organolithium reagents, metal amides, or metal hydrides.

7. A method according to claim 6, wherein in step (y), activation of the carboxylic group is achieved by reaction with pivalic acid chloride or chloroalkylformate in the presence of a base.

\* \* \* \* \*